United States Patent
Heemstra

(10) Patent No.: US 9,599,628 B2
(45) Date of Patent: *Mar. 21, 2017

(54) SMALL MOLECULE-DEPENDENT SPLIT APTAMER LIGATION

(71) Applicant: University of Utah Research Foundation, Salt Lake City, UT (US)

(72) Inventor: Jennifer M. Heemstra, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/064,532

(22) Filed: Mar. 8, 2016

(65) Prior Publication Data
US 2016/0258970 A1    Sep. 8, 2016

Related U.S. Application Data

(63) Continuation of application No. 14/288,240, filed on May 27, 2014, now Pat. No. 9,279,805, which is a continuation of application No. 13/534,988, filed on Jun. 27, 2012, now Pat. No. 8,735,367.

(60) Provisional application No. 61/501,632, filed on Jun. 27, 2011, provisional application No. 61/633,586, filed on Feb. 14, 2012.

(51) Int. Cl.
| | |
|---|---|
| *C12Q 1/68* | (2006.01) |
| *G01N 33/53* | (2006.01) |
| *G01N 33/94* | (2006.01) |
| *G01N 33/74* | (2006.01) |
| *C12N 15/115* | (2010.01) |

(52) U.S. Cl.
CPC ....... *G01N 33/9486* (2013.01); *C12N 15/115* (2013.01); *G01N 33/53* (2013.01); *G01N 33/5308* (2013.01); *G01N 33/743* (2013.01); *G01N 33/94* (2013.01); *G01N 33/946* (2013.01); *C12N 2310/16* (2013.01); *C12N 2310/351* (2013.01); *C12N 2320/10* (2013.01); *G01N 2400/00* (2013.01)

(58) Field of Classification Search
None
See application file for complete search history.

(56) References Cited

U.S. PATENT DOCUMENTS

| 7,799,554 B2 | 9/2010 | Mazumdar et al. |
|---|---|---|
| 2003/0224435 A1 | 12/2003 | Swelwert |
| 2006/0019406 A1 | 1/2006 | Wei et al. |
| 2006/0068500 A1 | 3/2006 | Wei et al. |
| 2006/0166222 A1 | 7/2006 | Lu et al. |
| 2008/0207883 A1 | 8/2008 | Janjic et al. |
| 2009/0030054 A1 | 1/2009 | Warmington et al. |
| 2010/0311820 A1 | 12/2010 | Layzer et al. |
| 2013/0065224 A1 | 3/2013 | Lu et al. |
| 2013/0164739 A1 | 6/2013 | Heemstra |

OTHER PUBLICATIONS

Glynou et al.; "Oligonucleotide-Functionalized Gold Nanoparticles as Probes in a Dry-Reagent Strip Blosensor for DNS Analysis by Hybridization," Analytical Chemistry; Jul. 15, 2003; pp. 4155-4160; vol. 75 No. 16; ACS Publications.

Liu, et al.; "A Simple and Sensitive 'Dipstick' Test I Serum Based on Lateral Flow Separation of Aptamer-Linked Nanostructures;" Angew. Chem. Int. Ed. 2006; vol. 45; pp. 7955-7959.

Sharma, et al.; "Enzyme-Linked Small-Molecule Detection using Split Aptamer Ligation"; Analytical Chemistry; published Jun. 18, 2012; American Chemical Society; pp. 6104-6109.

Sharma, et al.; "Small-Molecule-Dependent Split Aptamer Ligation"; J. Am. Chem. Soc., 133 (32), pp. 12426-12429; published Jul. 16, 2011.

Stojanovic, et al.; "Fluorescent Sensors Based on Aptamer Self-Assembly"; J. Am. Chem. Soc. Nov. 2, 2000; vol. 122; pp. 11547-11548.

Toubanaki, et al.; "Dry-Reagent Disposable Biosensor for Visual Genotyping of Single Nucleotide Polymorphisms by Oligonucleotide Ligation Reaction: Application to Pharmacogenetic Analysis;" Human Mutation 29(8), pp. 1071-1078; published online May 9, 2008 in Wiley InterScience.

Xu, et al.; "Aptamer-Functionalized Gold Nanoparticles as Probes in a Dry-Reagent Strip Biosensor for Protein Analysis"; Analytical Chemistry, vol. 81; No. 2; Jan. 15, 2009; pp. 669-675.

*Primary Examiner* — Tracy Vivlemore
(74) *Attorney, Agent, or Firm* — Thorpe North & Western, LLP; Todd B. Alder

(57) ABSTRACT

Methods, assays, and products for the detection of small molecules are provided. In one aspect, for example, a method of detecting a small molecule in a sample can include reacting together a first half of a DNA split aptamer having a first reactive group coupled thereto, a second half of a DNA split aptamer having a second reactive group coupled thereto, where the DNA split aptamer is selective for the small molecule, and a sample containing the small molecule. The first half and the second half bind to the small molecule and the first reactive group and the second reactive group react to form an aptamer ligation product of the first half and the second half. The method can also include assaying for the aptamer ligation product in order to detect the small molecule presence in the sample.

9 Claims, 9 Drawing Sheets

SEQUENCE LISTING

```
<160> NUMBER OF SEQ ID NOS: 20

<210> SEQ ID NO 1
<211> LENGTH: 24
<212> TYPE: DNA
<213> ORGANISM: Artificial sequence
<220> FEATURE:
<223> OTHER INFORMATION: completely synthesized

<400> SEQUENCE: 1
gttcttcaat gaagtgggac gaca                                          24

<210> SEQ ID NO 2
<211> LENGTH: 24
<212> TYPE: DNA
<213> ORGANISM: Artificial sequence
<220> FEATURE:
<223> OTHER INFORMATION: completely synthesized

<400> SEQUENCE: 2
cttcttcaac gaagtgggac gaca                                          24

<210> SEQ ID NO 3
<211> LENGTH: 34
<212> TYPE: DNA
<213> ORGANISM: Artificial sequence
<220> FEATURE:
<223> OTHER INFORMATION: completely synthesized

<400> SEQUENCE: 3
cttcttcaac gaagtgggac gacaaaaaaa aaaa                               34

<210> SEQ ID NO 4
<211> LENGTH: 34
<212> TYPE: DNA
<213> ORGANISM: Artificial sequence
<220> FEATURE:
<223> OTHER INFORMATION: completely synthesized
```

-continued

```
<400> SEQUENCE: 4
gtccttcaac gaagtgggac gacaaaaaaa aaaa                           34

<210> SEQ ID NO 5
<211> LENGTH: 13
<212> TYPE: DNA
<213> ORGANISM: Artificial sequence
<220> FEATURE:
<223> OTHER INFORMATION: completely synthesized

<400> SEQUENCE: 5
gggagtcaag aac                                                  13

<210> SEQ ID NO 6
<211> LENGTH: 13
<212> TYPE: DNA
<213> ORGANISM: Artificial sequence
<220> FEATURE:
<223> OTHER INFORMATION: completely synthesized

<400> SEQUENCE: 6
gggagtcaag aac                                                  13

<210> SEQ ID NO 7
<211> LENGTH: 24
<212> TYPE: DNA
<213> ORGANISM: Artificial sequence
<220> FEATURE:
<223> OTHER INFORMATION: completely synthesized

<400> SEQUENCE: 7
gttcttcaat gaagtgggac gaca                                      24

<210> SEQ ID NO 8
<211> LENGTH: 24
<212> TYPE: DNA
<213> ORGANISM: Artificial sequence
<220> FEATURE:
<223> OTHER INFORMATION: completely synthesized

<400> SEQUENCE: 8
cttcttcaac gaagtgggac gaca                                      24

<210> SEQ ID NO 9
<211> LENGTH: 24
<212> TYPE: DNA
<213> ORGANISM: Artificial sequence
<220> FEATURE:
<223> OTHER INFORMATION: completely synthesized

<400> SEQUENCE: 9
gctcttcaat gaagtgggac gaca                                      24

<210> SEQ ID NO 10
<211> LENGTH: 24
<212> TYPE: DNA
<213> ORGANISM: Artificial sequence
<220> FEATURE:
<223> OTHER INFORMATION: completely synthesized

<400> SEQUENCE: 10
gctcttcaac gaagtgggac gaca                                      24

<210> SEQ ID NO 11
```

```
<211> LENGTH: 24
<212> TYPE: DNA
<213> ORGANISM: Artificial sequence
<220> FEATURE:
<223> OTHER INFORMATION: completely synthesized

<400> SEQUENCE: 11
gtccttcaat gaagtgggac gaca                                          24

<210> SEQ ID NO 12
<211> LENGTH: 24
<212> TYPE: DNA
<213> ORGANISM: Artificial sequence
<220> FEATURE:
<223> OTHER INFORMATION: completely synthesized

<400> SEQUENCE: 12
gtccttcaac gaagtgggac gaca                                          24

<210> SEQ ID NO 13
<211> LENGTH: 24
<212> TYPE: DNA
<213> ORGANISM: Artificial sequence
<220> FEATURE:
<223> OTHER INFORMATION: completely synthesized

<400> SEQUENCE: 13
gcccttcaat gaagtgggac gaca                                          24

<210> SEQ ID NO 14
<211> LENGTH: 24
<212> TYPE: DNA
<213> ORGANISM: Artificial sequence
<220> FEATURE:
<223> OTHER INFORMATION: completely synthesized

<400> SEQUENCE: 14
gcccttcaac gaagtgggac gaca                                          24

<210> SEQ ID NO 15
<211> LENGTH: 13
<212> TYPE: DNA
<213> ORGANISM: Artificial sequence
<220> FEATURE:
<223> OTHER INFORMATION: completely synthesized

<400> SEQUENCE: 15
gggagtcaag aac                                                      13

<210> SEQ ID NO 16
<211> LENGTH: 13
<212> TYPE: DNA
<213> ORGANISM: Artificial sequence
<220> FEATURE:
<223> OTHER INFORMATION: completely synthesized

<400> SEQUENCE: 16
gggagtcaag aac                                                      13

<210> SEQ ID NO 17
<211> LENGTH: 16
<212> TYPE: DNA
<213> ORGANISM: Artificial sequence
<220> FEATURE:
<223> OTHER INFORMATION: Completely Synthesized

<400> SEQUENCE: 17
```

```
gggagtcaag aacgaa                                                        16

<210> SEQ ID NO 18
<211> LENGTH: 27
<212> TYPE: DNA
<213> ORGANISM: Artificial sequence
<220> FEATURE:
<223> OTHER INFORMATION: completely synthesized

<400> SEQUENCE: 18
acagcagggt gaagtaactt cttgctt                                            27

<210> SEQ ID NO 19
<211> LENGTH: 21
<212> TYPE: DNA
<213> ORGANISM: Artificial sequence
<220> FEATURE:
<223> OTHER INFORMATION: completely synthesized

<400> SEQUENCE: 19
taatatatga gggggtccat a                                                  21

<210> SEQ ID NO 20
<211> LENGTH: 20
<212> TYPE: DNA
<213> ORGANISM: Artificial sequence
<220> FEATURE:
<223> OTHER INFORMATION: completely synthesized

<400> SEQUENCE: 20
attatagcgg aggaaggtat                                                    20
```

SMALL MOLECULE-DEPENDENT SPLIT APTAMER LIGATION

PRIORITY DATA

This application is a continuation of U.S. patent application Ser. No. 14/288,240, filed May 27, 2014, now issued as U.S. Pat. No. 9,279,805, which is a continuation of U.S. patent application Ser. No. 13/534,988, filed on Jun. 27, 2012, now issued as U.S. Pat. No. 8,735,367, which claims the benefits of U.S. Provisional Patent Application Ser. No. 61/501,632, filed on Jun. 27, 2011, and of U.S. Provisional Patent Application Ser. No. 61/633,586, filed on Feb. 14, 2012, each of which are incorporated herein by reference in their entireties.

BACKGROUND OF THE INVENTION

Molecular recognition between DNA molecules has been shown to be a powerful tool for directing and promoting various chemical reactions. DNA-templated reactions have been utilized for a wide assortment of tasks, including ligation of complementary oligonucleotides, generating encoded libraries of complex small molecules, and detecting nucleic acids and proteins. However, such DNA-templated reactions are dependent upon the sequence defined affinity of the nucleic acid strands for one another.

SUMMARY OF THE INVENTION

The present disclosure provides methods, assays, and products for the detection of small molecules. In one aspect, for example, a method of detecting a small molecule in a sample can include reacting together a first half of a DNA split aptamer having a first reactive group coupled thereto, a second half of a DNA split aptamer having a second reactive group coupled thereto, where the DNA split aptamer is selective for the small molecule, and a sample containing the small molecule. The first half and the second half bind to the small molecule and the first reactive group and the second reactive group react to form an aptamer ligation product of the first half and the second half. The method can also include assaying for the aptamer ligation product in order to detect the small molecule presence in the sample.

A wide variety of small molecules can be detected according to the present techniques, and any such molecule is considered to be within the present scope. In one aspect, for example, the small molecule can be a controlled substance. In another aspect, the small molecule can be an opioid. In yet another aspect, the small molecule can be a steroid. In a further aspect, the small molecule can be cocaine.

Additionally, a variety of chemistries are contemplated that would be useful in ligating together split aptamer strands, and any such chemistry is considered to be within the present scope. In one aspect, for example, the first reactive group can be an azide and the second reactive group can be a cyclooctyne carboxylic acid, and the ligation product is a result of a strain-promoted azide-alkyne cycloaddition reaction. In another aspect, the first reactive group can be an azide, and the second reactive group can be either an alkyne or a phosphine. In yet another aspect, the first reactive group can be a tetrazine and the second reactive group can be an alkene.

Furthermore, any assay capable of detecting the presence of a ligated split aptamer is considered to be within the present scope. Non-limiting examples of such assays can include enzyme-linked assays, lateral flow assays, reaction-dependent fluorometric assays, and the like.

In another aspect, a method of stabilizing a small molecule-dependent aptamer assay is provided. Such an assay can include reacting together a first half of a DNA split aptamer having a first reactive group coupled thereto, a second half of a DNA split aptamer having a second reactive group coupled thereto, and the small molecule, where the DNA split aptamer is selective for the small molecule. The method can also include reacting the first reactive group and the second reactive group to form an aptamer ligation product of the first half and the second half and assaying for the aptamer ligation product to detect the small molecule presence in the sample.

In yet another aspect, a ligated DNA aptamer product is provided. Such an aptamer product can include a first half of a small molecule-selective DNA aptamer and a second half of the small molecule-selective DNA aptamer, where the first half and the second have are ligated together with a non-DNA linkage. A variety of non-DNA linkages are contemplated, and any linkage capable of such ligation is considered to be within the present scope. In one aspect, the linkage can be an azide/cyclooctyne carboxylic acid-derived linkage. In another aspect, the linkage can be an azide/alkyne linkage. In yet another aspect, the linkage can be an azide/phosphine linkage. In a further aspect, the linkage can be a tetrazine/alkene linkage.

DEFINITIONS OF TERMS

In describing and claiming the present invention, the following terminology will be used in accordance with the definitions set forth below.

The singular forms "a," "an," and, "the" can include plural referents unless the context clearly dictates otherwise. Thus, for example, reference to "a linkage" can include reference to one or more of such linkages, and reference to "an aptamer" can include reference to one or more of such aptamers.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint without affecting the desired result.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

DETAILED DESCRIPTION

The present disclosure provides novel techniques for using small molecule binding to direct a chemical reaction between two nucleic acid strands. This novel approach can utilize a DNA-templated reaction controlled by small-molecule binding rather than inherent Watson-Crick affinity between the DNA strands. The recognition element utilized to accomplish this task is a split aptamer, which is comprised of two nucleic acid strands that bind to one another in the presence of a specific small molecule target. Thus, in one aspect such a reaction can be a ligation between two fragments of a DNA split aptamer. For example, utilizing a split aptamer selective for cocaine and a strain-promoted azide-alkyne cycloaddition reaction, small molecule-dependent ligation that is dose-dependent over a wide range of cocaine concentrations has been achieved. It is noted that, while the term "small molecule" is used herein for convenience, the present scope extends to any molecule capable of being detected using a split aptamer technique.

Additionally, such ligation reactions are compatible with complex biological fluids such as, for example, human blood serum or urine. Moreover, studies of split aptamer ligation at varying salt concentrations and using structurally similar analogues of cocaine has revealed new insight into the assembly and small-molecule binding properties of the cocaine split aptamer. The ability to translate the presence of a small molecule target into a DNA ligation can be utilized as new broadly applicable small molecule detection assays.

In one aspect, strain-promoted azide-alkyne cycloadditions are examples of reactions that can be useful in split aptamer ligation because such chemistry does not significantly interfere with the small-molecule target and is compatible with complex biological fluids. Additionally, such chemistry is orthogonal to a wide assortment of functional groups and does not require additional reagents. It should be noted, however, that the present scope is not limited by the specific chemistries exemplified herein, nor is it limited by the specific exemplified small molecule species.

Figure 1:
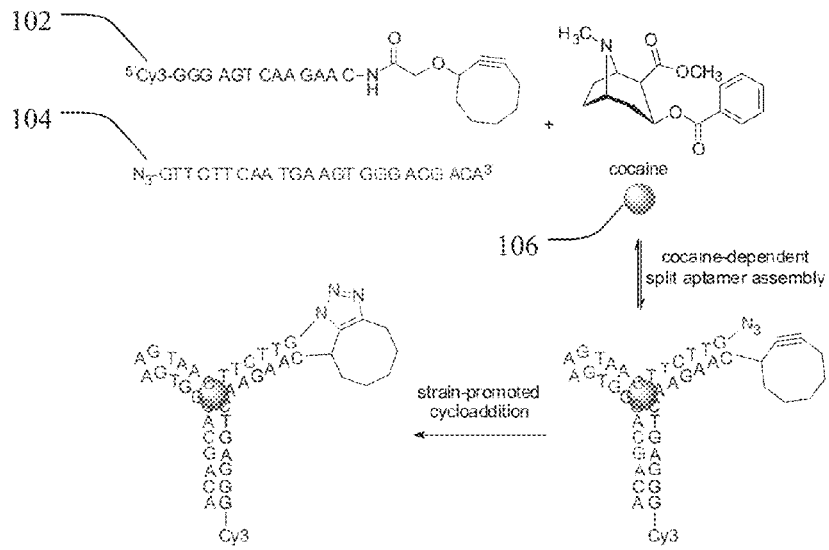
FIG. 1 is a schematic representation of Fragment A (102; SEQ ID NO 015) and Fragment B (102; SEQ ID NO 007) of a cocaine-selective DNA aptamer in accordance with one embodiment of the present invention.

As one example, as is shown in FIG. 1, one cocaine split aptamer Fragment A 102 is coupled with a cyclooctyne carboxylic acid and the other aptamer Fragment B 104 is coupled with an azide. Either of the fragments can additionally be functionalized with a visualization marker, such as, for example, a Cy3 fluorophore, thus enabling visualization of the ligation reaction by a suitable method such as denaturing polyacrylamide gel electrophoresis (PAGE). As can be seen in FIG. 1, cocaine 106 directs assembly of the split aptamer fragments 102 and 104 by positioning the azide and cyclooctyne in close proximity to one another. Such proximal positioning enhances the effective molarity of the reactants and can thus accelerate the templated cycloaddition relative to the untemplated background reaction.

Split aptamer assembly is an equilibrium process that is dependent in part upon the concentration of the small molecule. Thus, the templated ligation should proceed in a dose-dependent manner with respect to the small molecule. Denaturing PAGE can be used to monitor the reaction progress, as unligated fragments migrate farther on the gel relative to ligated fragments. Additionally, quantification of a visual marker such as Cy3 fluorescence can reveal the portion of the labeled fragment that has been incorporated into ligated product.

Figure 2:
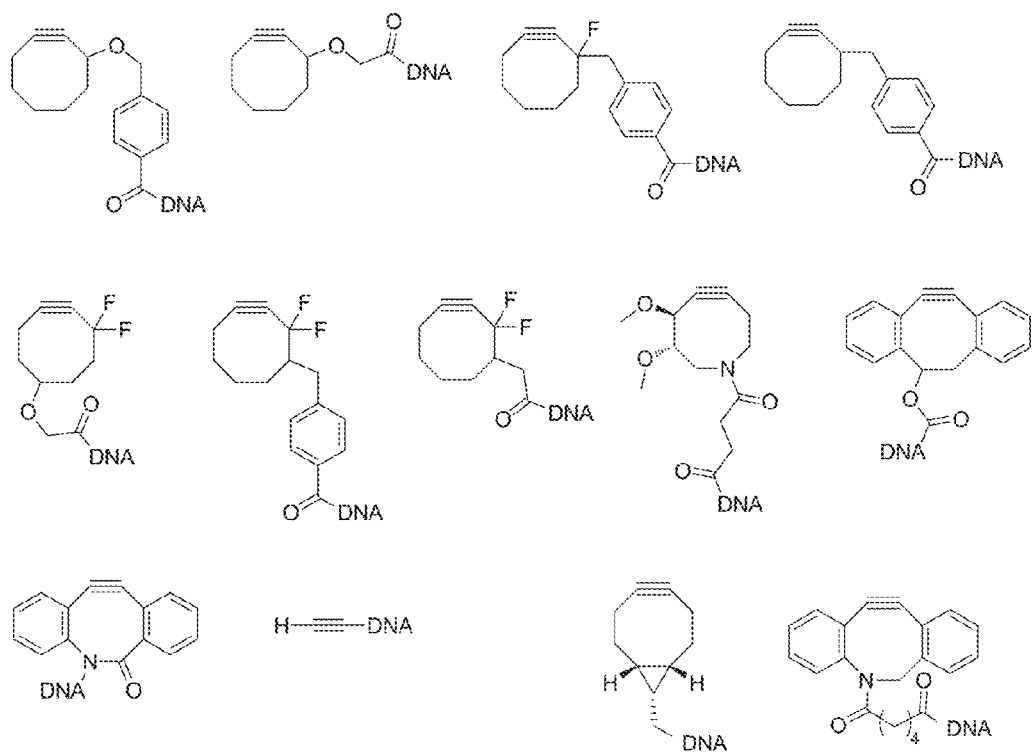
FIG. 2 shows reactive groups in accordance with another embodiment of the present invention.
Figure 3:
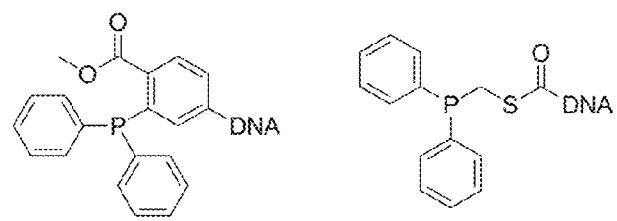
FIG. 3 shows reactive groups in accordance with another embodiment of the present invention.
Figure 4:
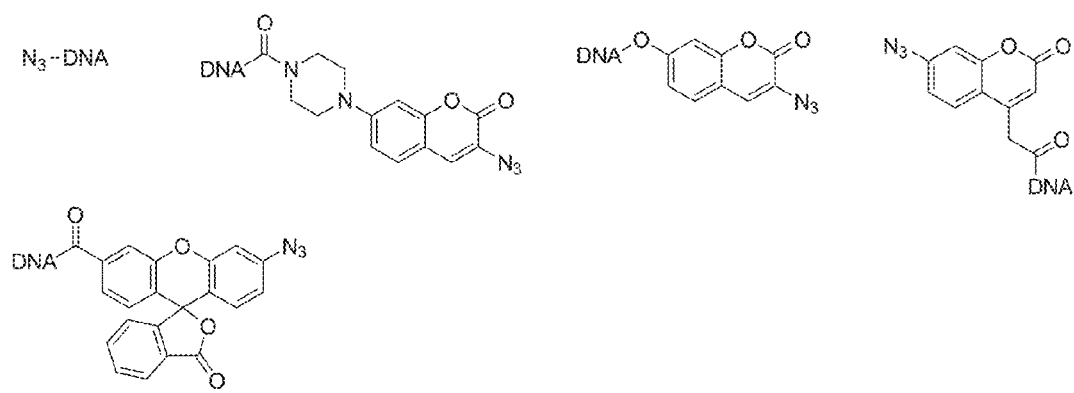
FIG. 4 shows reactive groups in accordance with another embodiment of the present invention.
Figure 5:
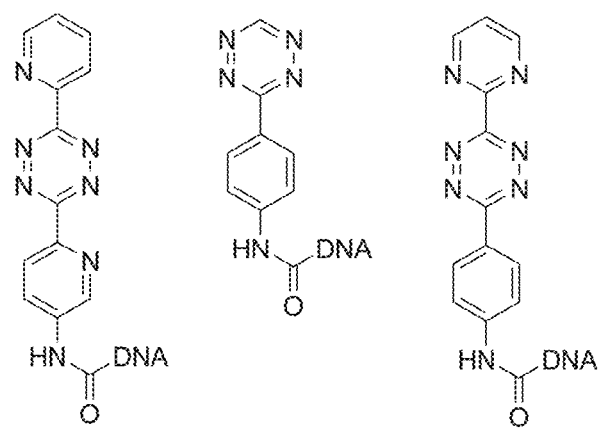
FIG. 5 shows reactive groups in accordance with another embodiment of the present invention.
Figure 6:
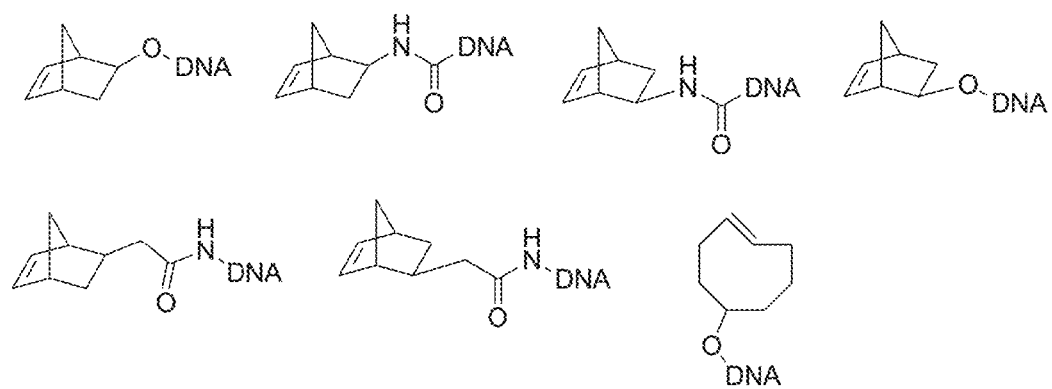
FIG. 6 shows reactive groups in accordance with another embodiment of the present invention.

As has been described, various chemistries can be utilized in ligation reactions to join split aptamers in a small molecule-dependent reaction, and any such chemistry is considered to be within the present scope. For example, in one aspect a strain-promoted azide-alkyne cycloaddition reaction between an azide and a cyclooctyne carboxylic acid can be utilized, as is described above. In other aspects, a ligation chemistry can be a reaction between an alkyne or a phosphine and an azide. Non-limiting examples of alkynes are shown in FIG. 2. Examples of phosphines are shown, without limitation, in FIG. 3. Non-limiting examples of azides are shown in FIG. 4. In another aspect, a ligation chemistry can be a reaction between a tetrazine and an alkene. Non-limiting examples of tetrazines are shown in FIG. 5, and non-limiting examples of alkenes are shown in FIG. 6.

Additionally, a DNA aptamer can be linked to a specified reactive group, both for the ligation chemistries described above and other chemistries not exemplified, with any known technique for making such a linkage. For example, such a linkage can be made using DNA functionalized with an amine, carboxylic acid, bromide, iodide, alcohol, or thiol functional group with or without an alkane or polyethyleneglycol spacer of 3-12 atoms in length.

Figure 7:
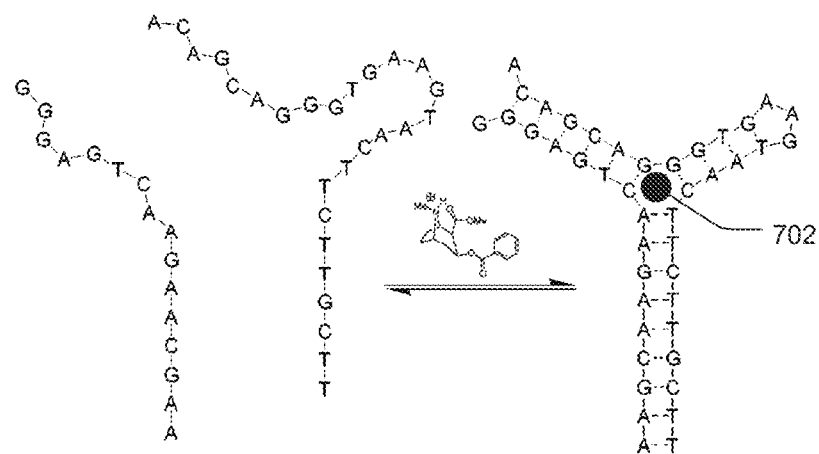
FIG. 7 shows a representation of a first fragment (SEQ ID NO 17; left) and a second fragment (SEQ ID NO 18; right) of a DNA aptamer in accordance with another embodiment of the present invention.
Figure 8:
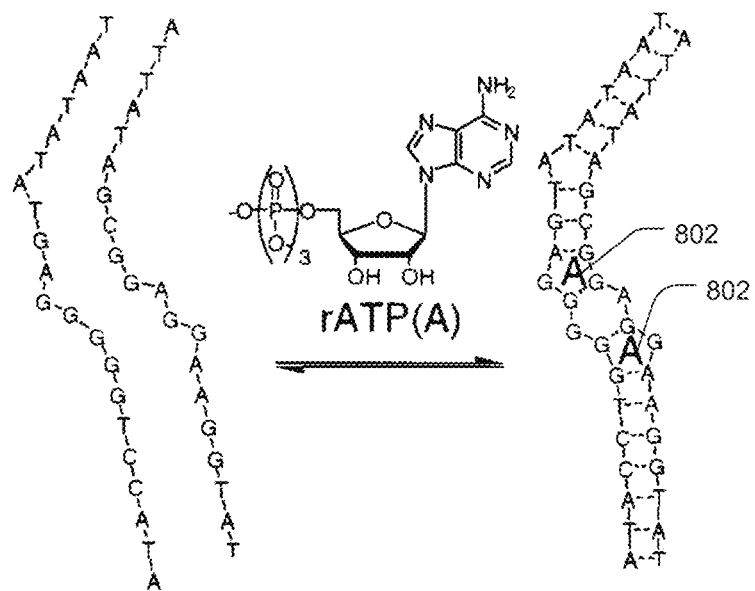
FIG. 8 shows a representation of a first fragment (SEQ ID NO 19; left) and a second fragment (SEQ ID NO 20; right) of a DNA aptamer in accordance with another embodiment of the present invention.

A variety of aptamers are contemplated for use with the present techniques, and any aptamer that shows small molecule-binding dependence is considered to be within the present scope. In other words, the present technique as described for cocaine molecules can be utilized with aptamers selective for other small molecules with potentially minor modifications. Accordingly, the aptamers disclosed herein are meant to be merely exemplary, and should not be seen as limiting the present scope. In one aspect, for example, an aptamer can be a cocaine-selective aptamer, as is shown in FIG. 7, where cocaine 702 is shown bound in the aptamer. In another aspect, as is shown in FIG. 8, an aptamer can be an ATP-selective aptamer, where ATP 802 is shown bound in the aptamer at A.

The present techniques can be utilized to detect numerous small molecules of interest, and as such, any small molecule capable of facilitating split aptamer ligation is considered to be within the present scope. In one aspect, for example, the small molecule can be a controlled substance. In another aspect, the small molecule can be an opioid. In yet another aspect, the small molecule can be a steroid. In a further aspect, the small molecule can be a narcotic. In yet a further aspect, the small molecule can be cocaine. Small molecules can also include metabolites and prodrugs of small molecules of interest. Other non-limiting examples of small molecules can include toxins, carcinogens, human and pathogenic metabolites, disease biomarkers, and the like.

A variety of assays are contemplated for the detection of ligated aptamers, and any such assay is considered to be within the present scope. Non-limiting examples of such assays can include enzyme-linked assays, lateral flow assays, fluorometric assays, colorimetric assays, electrophoretic assays, and the like.

In one aspect, for example, the assay can be an enzyme-linked assay. Aptamer-based analogues of "sandwich" enzyme-linked immunosorbent assay (ELISA) have been reported for protein detection. However, these assays are not directly applicable for small-molecule detection, as they rely on the ability of two separate aptamers to bind simultaneously to a protein target, and small molecules lack the surface area required to accommodate such interactions. While aptamers are not capable of forming the necessary "sandwich" interaction with small molecules, split aptamers are capable of this task, as they are comprised of two nucleic acid strands that only bind to one another in the presence of a specific small-molecule or protein target.

As one exemplary assay technique, an ELISA can utilize a reporter enzyme-chromogenic substrate format. Such an ELISA format can provide a convenient colorimetric output that is highly amenable to multiplexing for high-throughput analysis. One caveat, however, is that ELISA does require washing steps, during which signal can be degraded via interruption of target binding. This can be especially problematic for split aptamers, which have binding constants in the high μM range. The inventor has discovered a novel Split Aptamer Proximity Ligation (StAPL) technology in which attachment of reactive groups to the termini of split aptamer fragments enables translation of a small-molecule signal into the output of DNA ligation. As such, StAPL can be used to avert signal loss and thus be highly useful with a colorimetric split aptamer sandwich assay.

In a traditional sandwich ELISA, a capture antibody is covalently attached to a polystyrene microplate. If the target analyte is present, it binds to the capture antibody and recruits a detection antibody that is functionalized with a reporter enzyme such as horseradish peroxidase (HRP). A chromogenic substrate is then added, and is converted by HRP into an optically observable signal which can be quantified using an absorbance plate reader.

Figure 9:
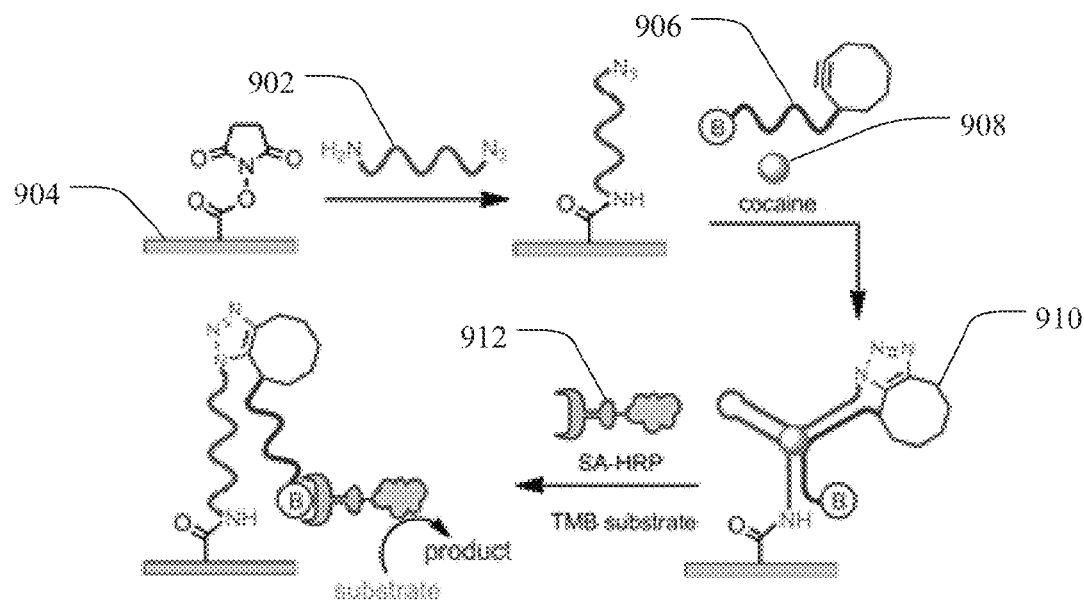
FIG. 9 is a schematic representation of an enzyme-linked cocaine-selective assay in accordance with one embodiment of the present invention.

To construct an aptamer-based sandwich assay for cocaine, the inventor utilized chemically-modified fragments of the cocaine split aptamer in place of the "capture" and "detection" antibodies used in traditional ELISA. While various chemistries are contemplated, as is described herein, in one aspect the capture strand can have an azide at one terminus and an amine at the opposite terminus, and the detection strand can have biotin at one terminus and a cyclooctyne at the opposite terminus. As is shown in FIG. 9, a capture strand 902 is attached to an N-hydroxysuccinimide (NHS)-functionalized microplate 904 via amide bond formation. Unreacted NHS groups on the microplate surface are then chemically blocked using bovine serum albumin (BSA). A test sample can then be added containing a detection strand 906 and varying concentrations of the cocaine target 908. If present, cocaine 908 directs assembly of the split aptamer fragments, bringing the azide and cyclooctyne groups into close proximity and thus promoting a cycloaddition to ligate the two fragments into a ligation product 910, which will be coupled to the microplate 904 surface. The resulting ligation yield is thus dependent upon cocaine concentration. As such, the concentration of cocaine present in the test sample is translated into dose-dependent covalent pull-down of biotin to the microplate surface. In the readout step, a streptavidin-HRP conjugate 912 is added, which binds to biotin and converts a colorless tetramethylbenzidine (TMB) substrate into an optically observable blue product. Additionally, the cocaine binding can be interrupted during washing steps without impacting the outcome of the assay, as the presence of cocaine is not required in the readout step due to the ligation of the fragments.

For the case of cocaine, the binding affinity of the cocaine split aptamer is low, at about 100 and the binding properties are highly susceptible to variables such as salt concentration. Thus, by ligating the aptamer strands via StAPL into a covalently bonded molecule upon cocaine binding, the detection sensitivity, the reproducibility, and the robustness of the assay is improved. The ligated product is indicative of a positive cocaine test, whether or not the cocaine is still bound to the aptamer in the assay. As such, using this assay the detection of cocaine at concentrations of 100 nM-100 µM in buffer and 1-100 µM human blood serum can be achieved. The detection limit of 1 µm in serum represents an improvement of two orders of magnitude over previously reported split aptamer-based sensors. As such, the StAPL process is an important aspect of the ELISA format. Additionally, the StAPL process can be utilized to improve detection sensitivity in a wide variety assay formats. Moreover, DNA split aptamers can be generated for a wide variety of small-molecule targets, making this research broadly applicable for detection of small-molecule analytes in biological samples.

EXAMPLES

As a general matter, unless otherwise noted, all starting materials were obtained from commercial suppliers and were used without further purification. Cocaine was purchased from Sigma-Aldrich as a 1 mg/mL solution in acetonitrile which was diluted with water, lyophilized, and redissolved in water at a concentration of 1 mg/mL. DIBAC (DBCO)-NHS ester was purchased from Click Chemistry Tools Inc. Clear NHS-functionalized DNA-BIND microplates were purchased from Fisher. Streptavidin-HRP conjugate (cat No. 21130) was purchased from Thermo scientific. TMB substrate (product code: TMBW) was purchased from SurModics (MN, USA). DNA was purchased from the University of Utah DNA/Peptide Synthesis Core Facility. Human blood serum was purchased from Aldrich. Mass. spectra were obtained through the Mass Spectrometry Core Facility, University of Utah. PAGE gels were analyzed for Cy3 fluorescence using a Typhoon 9400 scanner (Amersham Biosciences) with a 532 nm excitation laser and 580 BP 30 emission filter. Fluorescence volumes were corrected for background by subtracting the fluorescence volume of an identically sized area of the gel in which no bands were present. Absorbance values were recorded on a Biotek Synergy MX microplate reader. Regarding modifiers used for DNA synthesis, all modified phosphoramidites and CPG cartridges were purchased from Glen Research. Azide functionality was installed using bromohexyl phosphoramidite (10-1946), which was converted to azide on resin according to supplier protocols using NaI and $NaN_3$. Amine functionality was installed using C6-amino CPG cartridges (20-2956). Biotin functionality was installed using BiotinTEG phosphoramidite (10-1955). Cy3 functionality was installed using Cy3 phosphoramidite (10-5913).

Example 1

Cyclooctyne Modification of DNA

ALO carboxylic acid (Structure I) was coupled to amine-terminated DNA as described in A. K. Sharma, J. M. Heemstra, *J. Am. Chem. Soc.* 2011, 133, 12426-12429, which is incorporated herein by reference. MALDI-TOF (linear positive mode) calcd [M+H]+ 4949.1, found 4950.2.

A solution of DIBAC-NHS ester (Structure II, 100 µL, 200 mM in DMF) was added to a solution of DNA (350 µL, 85 µM in 100 mM sodium phosphate buffer, pH 7.2) in a 1.7 mL microcentrifuge tube. The reaction proceeded for 2 h at room temperature, then the reaction mixture was desalted using a NAP-5 column (GE Healthcare). DNA was purified using reverse phase HPLC (Agilent ZORBAX Eclipse XDB-C18, 5 µM particle size, 4.6×150 mM) with a binary mixture of 0.1 M TEAA:acetonitrile. MALDI-TOF (linear positive mode) calcd [M+H]+ 5158.5, found 5159.2.

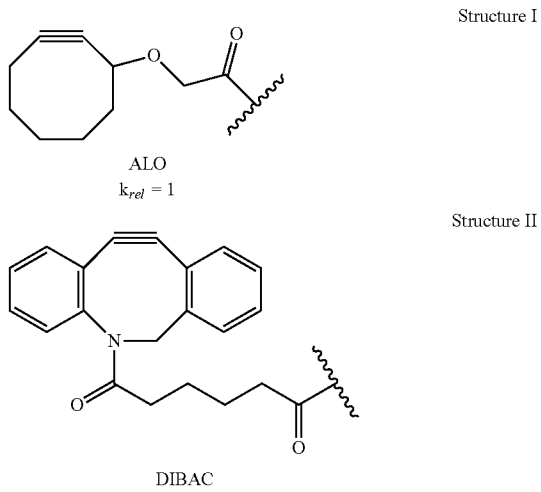

Structure I

ALO
$k_{rel} = 1$

Structure II

DIBAC
$k_{rel} = 240$

Example 2

Preparation of Microplate for Enzyme-Linked Assay

To each well of a 96-well NHS-functionalized DNA-BIND plate was added 100 µL of capture strand 1a (1 µM, see Table 1) in binding buffer (0.5 M NaPi, pH 8.5). The plate was agitated on a shaker for 24 h, then each well was washed with 3×100 µL wash buffer (10 mM NaPi, pH 7.4, 150 mM NaCl, 0.05% Tween 20) followed by 3×100 µL water. Unreacted NHS groups were blocked by addition of 100 µL blocking solution (3% BSA in binding buffer) to each well followed by incubation at 37° C. for 18 h. Each well was washed with 3×100 µL water, 3×100 µL wash buffer, then 3×100 µL water. The plate was wrapped in foil and stored dry at 4° C. until use.

TABLE 1

Split aptamer sequences used for enzyme-linked and solution-phase cocaine detection. Mutated bases are underlined.

| Number | Sequence (5'-3') |
|---|---|
| SEQ ID 01 (1a) | $N_3$-GTT CTT CAA TGA AGT GGG ACG ACA-$NH_2$ |
| SEQ ID 02 (1b) | $N_3$-<u>C</u>TT CTT CAA <u>C</u>GA AGT GGG ACG ACA-$NH_2$ |

TABLE 1-continued

Split aptamer sequences used for enzyme-linked and solution-phase cocaine detection. Mutated bases are underlined.

| Number | Sequence (5'-3') |
|---|---|
| SEQ ID 03 (1c) | $N_3$-CTT CTT CAA CGA AGT GGG ACG ACA-$A_{10}$-$NH_2$ |
| SEQ ID 04 (1d) | $N_3$-GTC CTT CAA CGA AGT GGG ACG ACA-$A_{10}$-$NH_2$ |
| SEQ ID 05 (2a) | Biotin-GGG AGT CAA GAA C-NH-ALO |
| SEQ ID 06 (2b) | Biotin-GGG AGT CAA GAA C-NH-DIBAC |
| SEQ ID 07 (3a) | $N_3$-GTT CTT CAA TGA AGT GGG ACG ACA |
| SEQ ID 08 (3b) | $N_3$-CTT CTT CAA CGA AGT GGG ACG ACA |
| SEQ ID 09 (3c) | $N_3$-GCT CTT CAA TGA AGT GGG ACG ACA |
| SEQ ID 10 (3d) | $N_3$-GCT CTT CAA CGA AGT GGG ACG ACA |
| SEQ ID 11 (3e) | $N_3$-GTC CTT CAA TGA AGT GGG ACG ACA |
| SEQ ID 12 (3f) | $N_3$-GTC CTT CAA CGA AGT GGG ACG ACA |
| SEQ ID 13 (3t) | $N_3$-GCC CTT CAA TGA AGT GGG ACG ACA |
| SEQ ID 14 (3h) | $N_3$-GCC CTT CAA CGA AGT GGG ACG ACA |
| SEQ ID 15 (4a) | Cy3-GGG AGT CAA GAA C-NH-ALO |
| SEQ ID 16 (4b) | Cy3-GGG AGT CAA GAA C-NH-DIBAC |

Example 3

Cocaine Detection Using Enzyme-Linked Assay

A 100 µL solution containing 100 pmol of detection strand 2a (see Table 1) along with the specified concentration of cocaine and buffer or serum was added to each microplate well. The plate was agitated on a shaker for the specified incubation time, then each well was washed with 3×100 µL water, 3×100 µL wash buffer, 3×100 water. 100 µL of SA-HRP solution (1:1000 streptavidin-HRP, 10% BSA in binding buffer) was added to each well, and the plate was agitated on a shaker for 1 h. Each well was washed with 3×100 µL water, 3×100 µL wash buffer, then 3×100 µL water. 100 µL of TMB solution was added to each well and the absorbance value read after 10 min (ALO) or 20 min (DIBAC) using an absorbance plate reader. Net absorbance values were calculated by subtracting the absorbance for a control having no cocaine present from the absorbance for each test solution.

Figure 10:
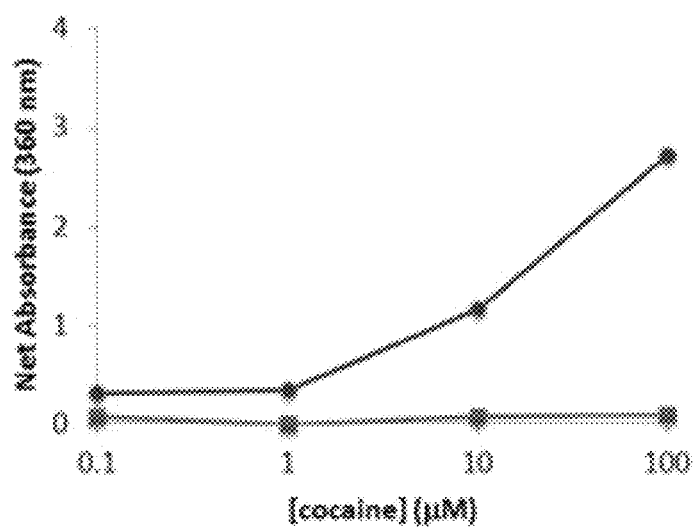
FIG. 10 is a graphical representation of data in accordance with one embodiment of the present invention.

In initial assay development, capture strand 1a and detection strand 2a were utilized (Table 1). In solution studies, ALO provided strong dose-dependent ligation after a reaction time of 4 h. However, in the microplate format, a 4 h incubation using strand 2a in the presence of cocaine concentrations as high as 100 µM provided no detectible ligation. The slower relative reaction kinetics in the microplate format may result from reduced accessibility of the azide strand when immobilized on the microplate surface. Extending the incubation time to 20 h provided dose-dependent ligation (FIG. 10). FIG. 10 shows results from enzyme-linked assays using capture strand 1a and ALO-functionalized detection strand 2a. Assays were tested using incubation time of 4 h (squares) or 20 h (circles). Conditions: 100 pmol 2a (1 µM), 25 mM Tris, pH 8.2, 5 mM NaCl.

Figure 11A:
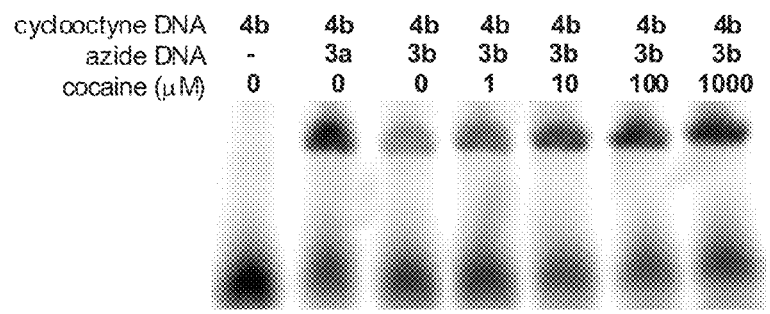
FIG. 11a shows ligation data in accordance with one embodiment of the present invention.
Figure 11B:
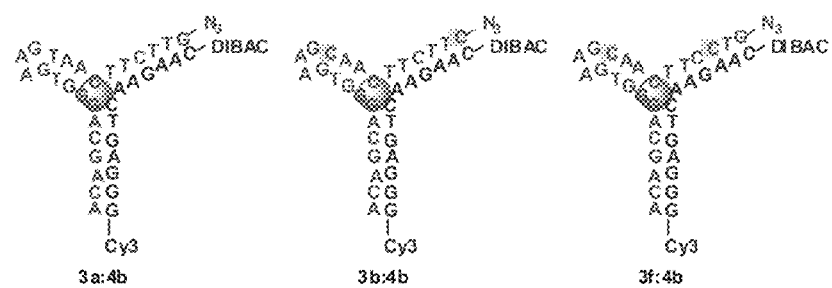
FIG. 11b shows aptamer binding structures (3a—SEQ ID NO 07; 4b—SEQ ID NO 16; 3b—SEQ ID NO 08; 3f—SEQ ID NO 12) in accordance with one embodiment of the present invention.

DIBAC reacts approximately 240-fold faster than ALO. Solution-phase reactions between DNA strands 3a and 4b (see Table 1) were performed to evaluate the suitability of DIBAC for use in cocaine-dependent split aptamer ligation. After a reaction time of 30 min, significant background ligation was observed in the absence of cocaine (FIG. 11a, lane 2). FIG. 11a shows that azide 3b reduces background ligation with DIBAC-functionalized 4b, but is capable of cocaine dose-dependent ligation. Conditions: 0.5 µM 4b, 2.0 µM 3a or 3b, 25 mM Tris, pH 8.2, 30 min. FIG. 11b shows base pairing in split aptamer sequences 3a:4b, 3b:4b, and 3f:4b. Mutated bases are highlighted.

Similar background ligation has been observed in the presence of human blood serum, where high salt concentrations can increase the affinity of the DNA strands for one another such that they anneal, and subsequently react, even in the absence of the small-molecule target. In the case of DIBAC, it is possible that the increased lipophilicity relative to ALO may be acting analogously to promote DNA annealing and subsequent ligation via hydrophobic packing interactions between the appended reactive groups. To overcome the background ligation with DIBAC, the azide strand was subtly mutated to 3b to decrease the inherent binding affinity of the split aptamer fragments for one another. Specifically, a GC base pair at the terminus of a duplex region was mutated to a CC mismatch and a GT wobble pair was mutated to a GC base pair (FIG. 11b). This net change of less than one base pair was sufficient to reduce the unwanted background ligation, but still enable dose-dependent ligation for cocaine concentrations of 1-100 µM in the solution phase (FIG. 11a, lanes 3-7).

Example 4

Solution-Phase Ligation Reactions

Solutions of DNA strands 3, 4, (see Table 1), and cocaine were diluted into 50 mM Tris buffer to give the final concentrations specified for each reaction. The reaction mixture was allowed to stand at room temperature for the specified reaction time, and then was diluted into 2× PAGE loading buffer containing 7M urea. The reaction mixture was separated by denaturing PAGE on a 12% TBE/urea polyacrylamide gel. Denaturing polyacrylamide gels were imaged as described above, and ligation yields were calculated using Equation 1:

$$\% \text{ Yield} = 100 * [VP/(VP+VR)] \quad [1]$$

in which VR is the fluorescence volume of the band for reactant strand 4 and VP is the fluorescence volume of the band for the strand 3+4 product.

Example 5

Calculation of Metabolite Cross-Reactivity

Solution-phase or enzyme-linked assays were carried out using cocaine, metabolite, or no small molecule. Ligation yield or absorbance at 360 nm was measured, and the percent cross-reactivity was calculated using Equation 2:

$$\% \text{ Cross-reactivity} = 100 * [(Ymet - Ynsm)/(Ycoc - Ynsm)] \quad [2]$$

in which Ymet is the yield or absorbance for reactions using metabolite, Ycoc is the yield or absorbance for reactions using cocaine, and Ynsm is the yield or absorbance for reactions with no small molecule present.

Example 6

Cocaine Detection Using Enzyme-Linked Assay—DIBAC

Figure 12:
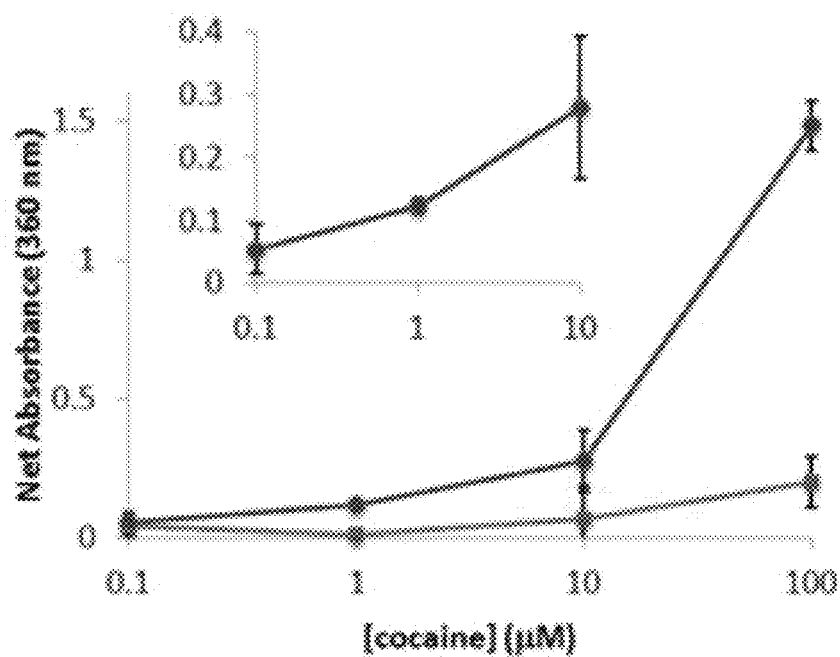
FIG. 12 is a graphical representation of data in accordance with one embodiment of the present invention.

Initial experiments using capture strand 1b (having the same sequence as 3b) and DIBAC-functionalized detection strand 2b showed only modest dose dependence after a 30 min incubation time. However, the use of capture strand 1c having an $A_{10}$ linker inserted between the aptamer sequence and the microplate resulted in vastly improved signal, presumably by providing increased access of the detection strand to the immobilized capture strand. As shown in FIG. 12, the enzyme-linked assay using capture strand 1c and DIBAC-functionalized detection strand 2b provided dose-dependent signal for cocaine concentrations of 100 nm-100 µM with a total assay time of less than 2 h. FIG. 12 shows an enzyme-linked assay using capture strand 1b (squares) or 1c (circles) and DIBAC-functionalized detection strand 2b. Conditions: 100 pmol 2b (1 µM), 25 mM Tris, pH 8.2, 5 mM NaCl, 30 min incubation time. Error bars represent standard deviation of three independent trials. Inset shows expansion of net absorbance at 360 nm for cocaine concentrations of 0.1-10 µM.

Example 7

Enzyme-Linked Assay for Cocaine Vs. Structurally Similar Metabolites

Figure 13:
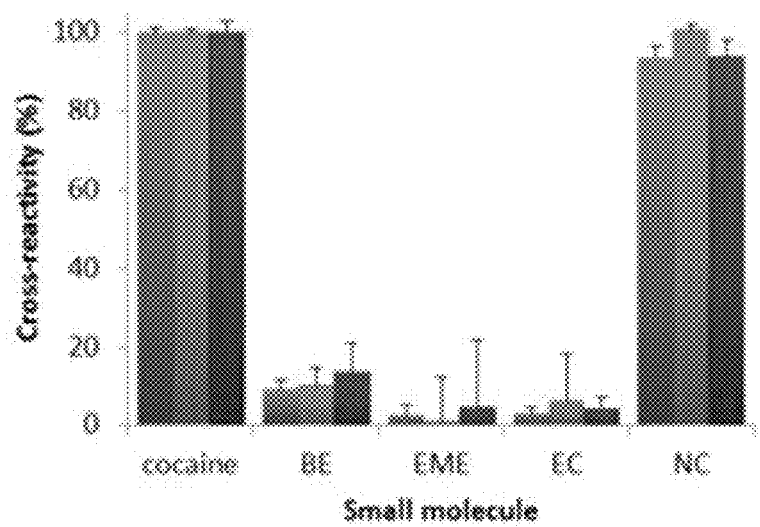
FIG. 13 is a graphical representation of data in accordance with one embodiment of the present invention.

The selectivity of the enzyme-linked assay for cocaine versus structurally similar metabolites was investigated. It is known that aptamer assembly is not significantly induced by ecgonine (EC), benzoylecgonine (BE), or ecgonine methyl ester (EME). However, norcocaine (NC) does bind to the split aptamer and induce ligation in the solution phase with yields nearly as high as those observed for cocaine. The following examines whether the selectivity of split aptamer ligation would be impacted by the sequence changes made to accommodate DIBAC (FIG. 11b) or by immobilization of the split aptamer in the microplate format. Solution-phase reactions and enzyme-linked assays were performed using sequences strands 3b:4b and 1c:2b, respectively, with 100 µM cocaine or metabolite. FIG. 13 compares metabolite cross-reactivity for solution-phase reactions using ALO- or DIBAC-functionalized split aptamer and enzyme-linked assays using DIBAC-functionalized split aptamer. As anticipated, EC, BE, and EME show low cross-reactivity, but NC gives nearly identical reactivity compared with cocaine. Importantly, the relative cross-reactivities for the DIBAC-functionalized split aptamer in solution or microplate format are not significantly different from those observed using the ALO-functionalized split aptamer in the solution phase. This demonstrates that selectivity of small-molecule detection is not affected by minor sequence changes or transition to the enzyme-linked format.

FIG. 13 shows metabolite cross-reactivity for solution-phase reactions using ALO-functionalized 3a:4a (left bar), solution-phase reactions using DIBAC-functionalized 3b:4b (middle bar), and enzyme-linked assays using DIBAC-functionalized 1c:2b (right bar). Conditions: 3a:4a—0.5 µM 4a, 2 µM 3a, 25 mM Tris, pH 8.2, 5 mM NaCl, 1 mM metabolite, 4h; 3b:4b—0.5 µM 4b, 2.0 µM 3b, 25 mM Tris, pH 8.2, 100 µM metabolite, 30 min; 1c:2b—100 pmol 2b (1 µM), 25 mM Tris, pH 8.2, 5 mM NaCl, 100 µM metabolite, 30 min incubation time. Error bars represent standard deviation of three (ALO) or four (DIBAC) independent trials.

Example 8

Enzyme-Linked Assay for Cocaine in Complex Biological Fluids

Figure 14A:
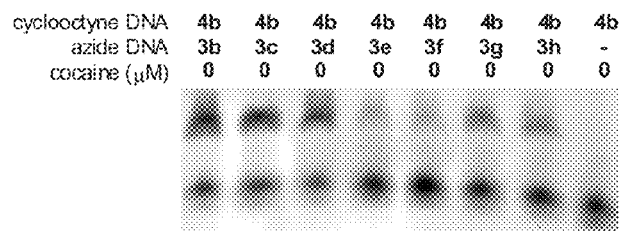
FIG. 14a shows ligation data in accordance with one embodiment of the present invention.

It can be useful for an aptamer-based assay to be capable of functioning not only in buffer, but also in complex biological fluids such as human blood serum. As noted above, the high salt concentration in serum can increase background ligation between the aptamer fragments. As is shown in FIG. 14a, lane 1, the DIBAC-functionalized 3b:4b aptamer sequence that had worked well in buffer gave significant background ligation when tested in 50% human blood serum. However, as also was described above, this background ligation can be circumvented via rational engineering of the split aptamer sequence, and thus a series of mutated azide strands (3c-h) were evaluated to identify a new sequence that would be compatible with both the DIBAC cyclooctyne and human blood serum (FIG. 14a, lanes 2-6). Strand 3f showed only minimal background ligation in solution phase reactions containing 50% serum, and thus was selected for use in the microplate format. In the sequence of 3f, an AT base pair is mutated to an AC mismatch. However, this mismatch is located near the middle of a duplex region, as opposed to at the end of a duplex region, as is the case for 3b. Thus, the mutation in 3f causes a bulge, rather than a fray, leading to a more pronounced impact on binding affinity between the split aptamer fragments (FIG. 11b). Sequence 3f also has the GT wobble pair to GC base pair mutation that was used in 3b.

Figure 14B:
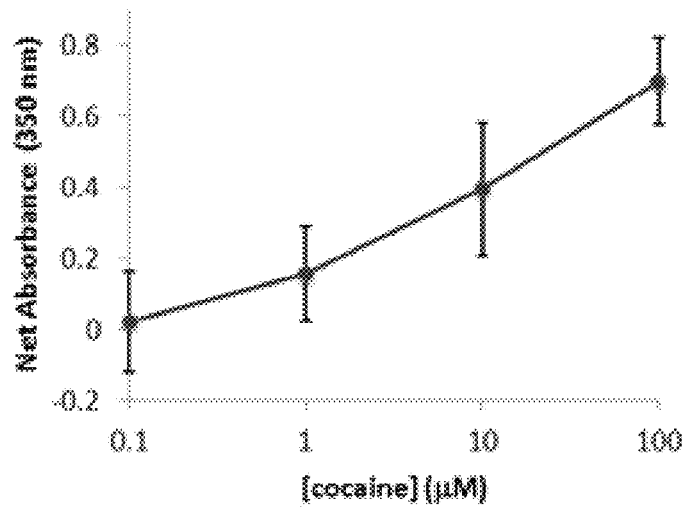
FIG. 14B shows a graphical representation of dose-dependent signal data in accordance with one embodiment of the present invention.

To test the ability of re-engineered azide sequence 3f to support enzyme-linked cocaine detection in serum, an $A_{10}$ linker was appended to 3f to give capture strand 1d. Strand 1d was then utilized with DIBAC-functionalized detection strand 2b to perform the enzyme-linked assay in 50% human blood serum. The data in FIG. 14b show dose-dependent signal for cocaine concentrations of 100 nM-100 µM. The signal for 100 nM cocaine is above the baseline, but not outside of error. Thus, the detection limit of the enzyme-linked assay is 1 µM for cocaine in human blood serum. However, the detection of 1 µM cocaine in serum represents a 10-fold improvement relative to previous solution phase-studies, and a 100-fold improvement relative to the best reported split aptamer sandwich assay.

FIG. 14a shows screening of azide sequences 3b-h in solution phase to reduce background ligation with DIBAC-functionalized 4b in serum. Conditions: 0.5 µM 4b, 2.0 µM 3b-h, 50% human blood serum in water, 30 min. FIG. 14b shows enzyme-linked assay in human blood serum using capture strand 1d and DIBAC-functionalized detection strand 2b. Conditions: 100 pmol 2b (1 µM), 75 mM NaCl, 50% serum 30 min incubation time. Error bars represent standard deviation of three independent trials.

Example 9

Enzyme-Linked Assay

One split aptamer half having a 3' amine and 5' azide was immobilized covalently on a DNA-BIND 96-well plate (Corning) that is functionalized with NHS esters. The plate was washed with buffer, and excess NHS esters blocked with BSA (attachment, washing, and blocking steps according to manufacturer's instructions). The sample to be tested was added to the wells in the plate along with the second aptamer half bearing a 5' biotin and 3' cyclooctyne. If the small molecule is present in the sample, it will promote ligation of the biotinylated DNA to the DNA strand immobilized on the plate via reaction between the azide and cyclooctyne. The plate was then washed and streptavidin-horseradish conjugate was added. After again washing, horseradish peroxidase (HRP) substrate (for example, TMB) was added and the results obtained using a UV plate reader.

Example 10

Lateral Flow Assay

The lateral flow biosensor was constructed as described in: Glynou et al., 2003, Oligonucleotide-functionalized gold nanoparticles as probes in a dryreagent strip biosensor for DNA analysis by hybridization. Anal Chem 75:4155-4160, which is incorporated herein by reference. $T_{30}$ DNA-functionalized gold nanoparticles were spotted on a conjugation pad. One split aptamer half was functionalized with a 3' $A_{30}$ sequence and a 5' azide. The second aptamer half was functionalized with a 5' biotin and 3' cyclooctyne. Both aptamer halves were spotted on the conjugation pad just below the gold nanoparticles. The test zone was spotted in one location with streptavidin and in another location with poly-dA DNA.

The lateral flow device was placed in a sample to be tested. If the target small molecule is present, it will promote ligation of the two aptamer halves, generating a DNA molecule having both $A_{30}$ and biotin. This molecule is then bound to the gold nanoparticles as it migrates up the sensor. When the molecules reach the test zone, the biotin will bind to the streptavidin and remaining gold nanoparticles will bind to the poly-dA. The gold nanoparticles are visually observable by their bright red color. If the small molecule is present and has promoted ligation, the gold nanoparticles will form a red line at both the streptavidin and poly-dA test zones, indicating a positive result. If no split aptamer ligation occurs, the gold nanoparticles will not be conjugated to biotin and will thus only form a red line at the poly-dA test zone, indicating a negative test.

Example 11

Cocaine-Dependent Split Aptamer Ligation

Figure 15A:
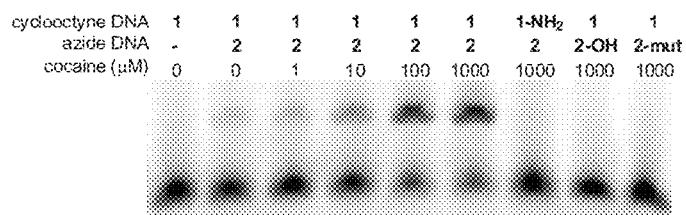
FIG. 15A shows ligation data in accordance with another embodiment of the present invention.
Figure 15B:
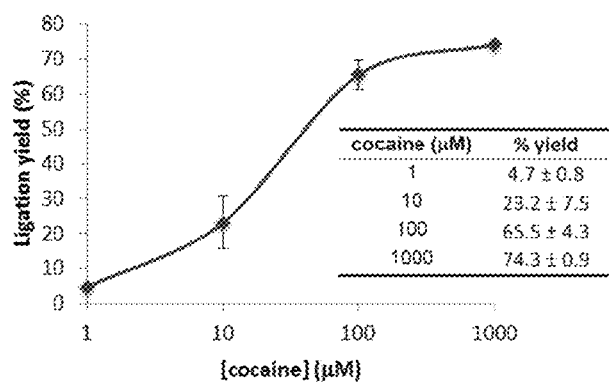
FIG. 15B shows a graphical representation of dose-dependent signal data in accordance with one embodiment of the present invention.

Returning to the discussion of the cocaine-dependent split aptamer case, FIGS. 15a and b show that the templated ligation proceeds in a dose-dependent manner for cocaine concentrations of 1 μM-1 mM, providing ligation yields of 5-74%. FIG. 15a shows a denaturing PAGE of ligation reactions. The lower bands represent unreacted strand 1 and upper bands represent 1+2 ligated product. Conditions for this particular example were 0.5 μM 1, 2.0 μM 2, 25 mM Tris, pH 8.2, 5 mM NaCl, 4h. FIG. 15b shows yield of ligated product as a function of cocaine concentration. Errors represent standard deviation of three independent trials. As can be seen in FIG. 15, no reaction is observed when the cyclooctyne (1-NH$_2$) or azide (2-OH) is omitted or one base is mutated in the azide strand (2-mut). These controls demonstrate that cocaine-dependent assembly of the split aptamer is sequence-specific and that ligation proceeds via reaction between the azide and cyclooctyne functional groups.

Figure 16:
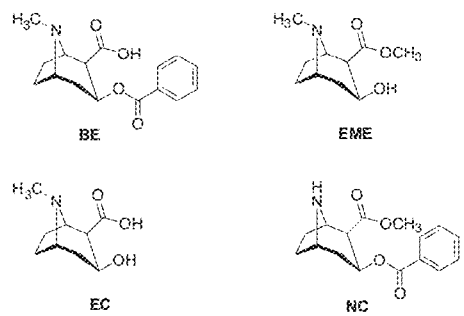
FIG. 16 shows data in accordance with another embodiment of the present invention.
Figure 16:
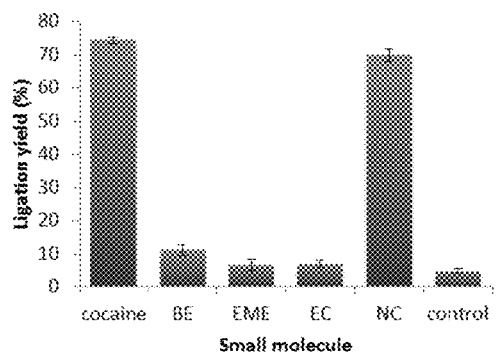

Similar to the data shown in FIG. 11, and described in Example 7, the selectivity of the split aptamer ligation for cocaine versus its structurally similar metabolites was next investigated. Previous studies using the cocaine split aptamer have demonstrated that aptamer assembly is not significantly induced by benzoylecgonine (BE) or ecgonine methyl ester (EME). Binding of ecgonine (EC) by the split aptamer has not been studied, but the regular cocaine aptamer has been shown to selectively bind cocaine over ecgonine. Thus, it is anticipated that the split aptamer ligation would not be strongly promoted by BE, EME, or EC. There appear to be no reports on the selectivity of the cocaine aptamer or split aptamer for the metabolite norcocaine (NC) in which the bridge nitrogen is demethylated. As shown in FIG. 16, reactions using 1 mM BE, EME, or EC result in nominal ligation yields of 11, 7, and 7% respectively. FIG. 16 shows the selectivity of split aptamer ligation for cocaine versus metabolites. Conditions for this particular example are 0.5 μM 1, 2.0 μM 2, 25 mM Tris, pH 8.2, 5 mM NaCl, 1 mM metabolite, 4h. Control is same conditions as above in FIG. 9, but with no cocaine or metabolite. Error bars represent+/−standard deviation of three independent trials.

This indicates that both the methyl ester and benzoyl group may be necessary for binding of the small molecule to the split aptamer. Interestingly, it is noted that 1 mM NC did in fact promote the ligation reaction, giving a yield of 70%, only 4% less than the yield observed with cocaine. This result suggests that the methyl group of the bridge nitrogen does not play a significant role in recognition of cocaine by the split aptamer. Curiously, the overall tolerance of the split aptamer to cocaine modification is similar to the tolerance of the biological receptors that cocaine targets in vivo, as norcocaine is the only reported cocaine metabolite shown to be pharmacologically active.

Figure 17A:
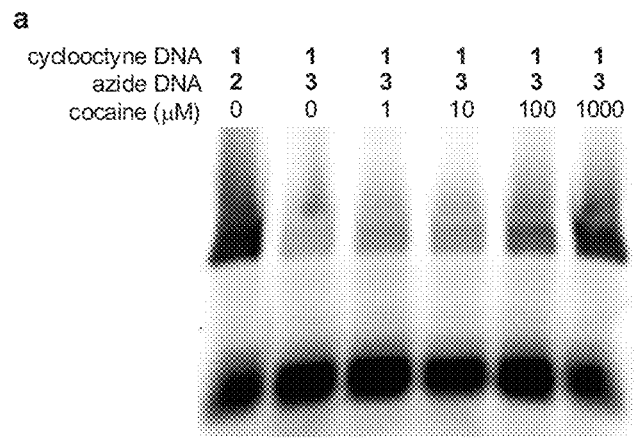
FIG. 17a shows ligation data in accordance with another embodiment of the present invention.

One goal of the present work is the application of small-molecule-dependent split aptamer ligation toward the development of new assays for sensing drug molecules and metabolites in biological samples. Thus, it can be beneficial to establish whether the templated ligation would be compatible with human blood serum. DNA aptamers 1 and 2 are incubated in the same buffered solution used in the experiments above (e.g. 25 mM Tris, pH 8.2, 5 mM NaCl), but having 20% added serum. PAGE analysis reveals significant ligation even in the absence of cocaine (FIG. 17a, lane 1). Earlier studies of the ligation in buffer had revealed that increasing the concentration of NaCl in the reaction mixture led to increasing degrees of background ligation. It is thus hypothesized that higher salt concentrations increase the affinity of the DNA strands for one another such that they can anneal, and subsequently react, even in the absence of the small-molecule target. Given this observation and the fact that sodium ion concentration in normal human serum is 137-147 mM, it is not entirely surprising to observe significant background reaction in 20% serum.

Rather than further dilute the blood serum, it was hypothesized that the split aptamer could be re-engineered to be more "salt tolerant" by converting one or more base pairs to mismatches. This may lower the inherent affinity of the DNA strands, presumably compensating for the increased driving force for annealing that is imparted by the higher salt concentration. Eight azide strands were screened having varying levels of mutation, and it was found that DNA 3 was sufficiently mutated to drastically reduce the undesired background reactivity yet retain the ability to assemble and react with 1 in the presence of cocaine (FIG. 17). In strand 3, one GC base pair is mutated to a CC mismatch. However, this negative effect is partially compensated for by mutating a GT wobble pair to a GC base pair. These results speak to the tunability of split aptamer assembly, as only a subtle change to the level of base pairing was necessary to dramatically alter the binding properties of the DNA strands.

Using mutated DNA 3, cocaine dose-dependent ligation is demonstrated with 1 in a sample containing 20% human blood serum (FIG. 17a, lanes 2-6). Interestingly, PAGE does not show any evidence of nuclease degradation of the DNA strands. However, lower yields for the cocaine-dependent ligation are not observed in the buffer-serum mixture compared with buffer alone. This is likely a result of cocaine hydrolysis by serum esterases, as cocaine is known to be rapidly metabolized in vivo to BE and EME, neither of which is capable of promoting the ligation reaction.

Figure 17B:
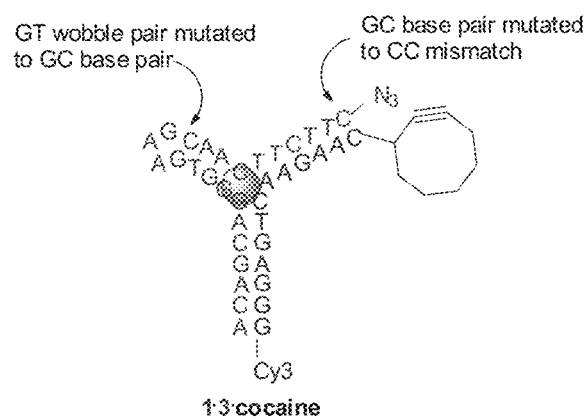
FIG. 17b shows a first fragment (SEQ ID NO 02; left) and a second fragment (SEQ ID NO 15; right) of a cocaine split aptamer in accordance with another embodiment of the present invention.

FIG. 17a shows denaturing PAGE of ligation reactions in human blood serum. Conditions for this example are 0.5 µM 1, 2.0 µM 2 or 3, 25 mM Tris, pH 8.2, 5 mM NaCl, 20% serum, 8h. FIG. 17b shows that the mutant sequence 3 has two mutated bases, which impart a net negative effect on duplex formation with 1.

Using the cocaine split aptamer, it is thus reported here the first example of a DNA-templated reaction that is dependent upon small-molecule binding rather than inherent Watson-Crick affinity. This templated ligation is dose-dependent for cocaine concentrations of 1 µM-1 mM in buffer and 10 µM-1 mM in human blood serum. Studies of the templated reaction under varying conditions has revealed the salt sensitivity of split aptamer assembly, and has enabled the re-engineering of a more "salt tolerant" cocaine split aptamer sequence. Additionally, studies of the split aptamer ligation using cocaine metabolites in which the main functional groups are systematically modified has revealed new insight into the interaction of the split aptamer with cocaine.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. An assay for detecting a small molecule in a sample, comprising:
   a first half of a DNA split aptamer having a first reactive group coupled thereto;
   a second half of a DNA split aptamer having a second reactive group coupled thereto, wherein the DNA split aptamer is selective for the small molecule, and wherein the first half and the second half are operable to selectively bind to the small molecule and to react to form an aptamer ligation product of the first half and the second half; and
   an assay mechanism operable to detect the ligation product.

2. The assay of claim 1, wherein the first reactive group is an azide and the second reactive group is a cyclooctyne carboxylic acid and the ligation product is a result of a strain-promoted azide-alkyne cycloaddition reaction.

3. The assay of claim 1, wherein the first reactive group is an azide, and the second reactive group is either an alkyne or a phosphine.

4. The assay of claim 1, wherein the first reactive group is a tetrazine and the second reactive group is an alkene.

5. The assay of claim 1, wherein the small molecule includes a member selected from the group consisting of a controlled substance, an opioid, and a steroid.

6. The assay of claim 1, wherein the assay mechanism is an enzyme-linked assay mechanism.

7. The assay of claim 1, wherein the assay mechanism is a lateral flow assay mechanism.

8. The assay of claim 1, wherein the assay mechanism is a reaction-dependent fluorometric assay.

9. The assay of claim 1, wherein the small molecule is cocaine.

* * * * *